United States Patent [19]

Bauer et al.

[11] Patent Number: 5,098,965
[45] Date of Patent: Mar. 24, 1992

[54] PROCESS FOR PREPARING LOW-CHLORINE EPOXY RESINS

[75] Inventors: Ronald S. Bauer; Kailash C. B. Dangayach, both of Houston, Tex.

[73] Assignee: Shell Oil Company, Houston, Tex.

[21] Appl. No.: 648,778

[22] Filed: Jan. 31, 1991

[51] Int. Cl.$^5$ .................. C08G 59/06; C08G 59/08
[52] U.S. Cl. .................... 525/507; 528/90; 528/93; 528/95; 528/98
[58] Field of Search ............. 525/507, 385, 534; 528/89, 90, 93, 95, 98; 549/514, 515, 516, 517

[56] References Cited

U.S. PATENT DOCUMENTS

| | | | |
|---|---|---|---|
| 3,013,087 | 12/1961 | Schwarzer | 568/270 |
| 4,153,621 | 5/1979 | Hartmann | 549/560 |
| 4,661,644 | 4/1987 | Silvis | 568/723 |
| 4,722,983 | 2/1988 | Monnier | 525/507 |
| 4,778,863 | 10/1988 | Wang | 525/507 |
| 4,785,061 | 11/1988 | Wang | 525/507 |

Primary Examiner—John Kight, III
Assistant Examiner—Shelley A. Wright

[57] ABSTRACT

A process is disclosed for preparing a low-chlorine epoxy resin which employs crystallization of the epoxy from solution in a finishing step of the preparation process. The process involves (a) contacting, in a basic reaction medium, epichlorohydrin and a biphenol to produce a reaction product mixture containing a diglycidyl ether of the biphenol; (b) dissolving the diglycidyl ether in an organic solvent and, optionally, contacting the diglycidyl ether with a dehydrochlorination agent; and (c) reducing the temperature of the organic solvent so as to effect crystallization of a low-chlorine fraction of the diglycidyl ether.

24 Claims, No Drawings

PROCESS FOR PREPARING LOW-CHLORINE EPOXY RESINS

BACKGROUND OF THE INVENTION

This invention relates to the production of epoxy resins. In one aspect, the invention relates to the production of low-chlorine diglycidyl ether of biphenols suitable for electronics applications.

Epoxy resins are used in the electronics industry for encapsulating semiconductors and other sensitive electronic parts. Encapsulation formulations typically contain an epoxy resin, a curing agent and a filler material such as silica. In the encapsulation process, the electronic part is cast with a molten encapsulation formulation which is then subjected to conditions effective to cure the epoxy resin. The resulting cured resin provides physical integrity and environmental protection for the encapsulated part.

The epoxy resin used in encapsulation formulations must meet a demanding set of criteria, including low melt viscosity and low chlorine content. Diglycidyl ethers of biphenols, such as the reaction products of epichlorohydrin and biphenols, for example, have low melt viscosity and are useful in encapsulation, but these resins typically have residual chlorine levels in excess of 1000 ppm. This residual chlorine can, particularly at the high-temperature conditions which exist in current high-performance electronic systems, corrode metal parts of the underlying electronic component and will cause eventual failure of the part.

It is therefore an object of the invention to provide a process for preparing epoxy resins. In one aspect, it is an object of the invention to prepare low-chlorine epoxy resins suitable for high-performance electronics applications.

BRIEF SUMMARY OF THE INVENTION

According to the invention, a process is provided for preparing a diglycidyl ether of a biphenol, the process comprising (a) contacting, in a reaction mixture comprising a basic condensation catalyst, epichlorohydrin and a phenolic compound which can be described by the formula

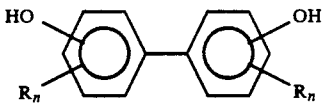

in which each R is selected independently from hydrogen, $C_{1-5}$ alkyl and halide and n is a number within the range of 0 to 4, to produce a reaction product mixture comprising unreacted epichlorohydrin, by-product salt and a diglycidyl ether of the biphenol; (b) removing unreacted epichlorohydrin and by-product salt; (c) dissolving the crude diglycidyl ether in an organic solvent at a temperature of at least about 60° C.; (d) reducing the temperature of the solution to effect crystallization of a relatively low-chlorine fraction of the diglycidyl ether; and (e) recovering the crystallized diglycidyl ether. Crystallization of the diglycidyl ether directly from the solvent has been found to produce a resin significantly lower in chlorine content than that recovered by conventional evaporation of the solvent from the resin solution.

DETAILED DESCRIPTION OF THE INVENTION

The invention process involves preparation of a low-chlorine diglycidyl ether of a biphenol (hereinafter, "epoxy resin") by crystallization of the epoxy resin from solution in a finishing step of the process. The polyglycidyl epoxy resin is composed of a mixture of glycidated products the major portion of which is the diglycidyl species which can be described by the general formula

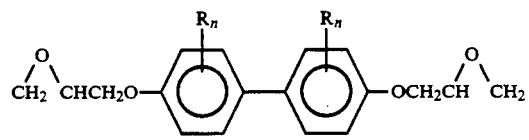

in which each R is selected independently from hydrogen, $C_{1-5}$ alkyl, preferably methyl and ethyl, and halide, preferably chloride and bromide. Such epoxy resins include, for example, diglycidly ethers of 4,4'-dihydroxybiphenyl, 3,3'-dimethyl-4,4'-dihydroxybiphenyl, 3,3',5,5'-tetrabutyl-4,4'-dihydroxybiphenyl, 3,3'-dimethyl-5,5'-dibromo-4,4'-dihydroxybiphenyl, 3,3'5,5'-tetrabromo-4,4'-dihydroxybiphenyl, 3,3',5,5'-tetramethyl-4,4'-dihydroxybiphenyl.

Such epoxy resins are generally prepared in a two-step process involving the base-catalyzed condensation reaction of a biphenol with a haloalkylene oxide such as epichlorohydrin, followed by a dehydrohalogenation step in which easily-hydrolyzable chloride is removed from the epoxyfunctional condensation product of the first step. The condensation reaction is carried out in a reaction mixture containing a substantial excess of the epichlorohydrin and an optional organic solvent at a temperature within the range of about 60° to about 110° C. over a period within the range of about 1 to about 5 hours. The epichlorohydrin is typically present in the reaction mixture in a molar ratio with respect to phenolic hydroxyls within the range of about 2:1 to about 20:1, preferably about 4:1 to about 12:1. The preferred basic condensation catalyst is an alkali metal hydroxide such as sodium hydroxide, potassium hydroxide or lithium hydroxide, for example. The base is usually added to the reaction mixture as an aqueous solution in a concentration of about 20 to about 60, preferably about 30 to about 50, percent by weight. The base is generally employed in an amount of about 0.8 to about 1.4 moles per mole of phenolic hydroxyl and is added in increments during the course of the condensation reaction.

The condensation reaction can be carried out in an organic solvent such as a ketone, alcohol, glycol ether, polar aprotic liquid, aromatic hydrocarbon or aliphatic hydrocarbon, including such specific examples as methyl ethyl ketone, methyl isobutyl ketone, methanol, isopropyl alcohol, dimethyl sulfoxide, dimethylformamide, and the like.

The condensation reaction product mixture includes the glycidated biphenol, excess epichlorohydrin, excess base and by-product alkali metal chloride. The reaction product mixture is filtered or siphoned for removal of solids and excess base and is distilled for removal of volatiles such as the excess epichlorohydrin and any organic solvent.

The remaining crude epoxy resin contains a high level of residual chlorine which must be reduced for utility of the resin in electrical applications. The crude resin is treated by the invention finishing method for recovery of a low-chlorine fraction of the diglycidyl ether, optionally via a dehydrohalogenation process step. In the latter option, the crude resin is treated for removal of at least a portion of easily-hydrolyzable chloride ions by contact, in an organic solvent, with a dehydrohalogenation agent such as an aqueous alkali metal hydroxide or aqueous alkali metal alkoxide, for example. Specific dehydrochlorination agents include aqueous sodium hydroxide, potassium hydroxide and potassium tert-butoxide, for example. Suitable organic solvents include ketones, alcohols and aromatic hydrocarbons, with ketones such as methyl ethyl ketone and methyl isobutyl ketone currently preferred because of the effectiveness of these solvents both for dehydrochlorination and as a crystallization medium for the polyfunctional epoxy resin. A co-solvent such as an alcohol can be employed so long as it does not significantly interfere with subsequent crystallization of the epoxy resin. The currently-preferred co-solvent is isopropyl alcohol.

The dehydrochlorination step is typically carried out at an elevated temperature within the range of about 60° to about 110° C., preferably about 80° to about 100° C., over a time of at least about 0.5 hour, preferably about 1 to about 4 hours. The dehydrochlorination product mixture includes the epoxy resin in solution and an aqueous phase containing excess dehydrochlorination agent and by-product salt, which are removed by suitable means such as filtration or siphoning.

Alternatively, the crude diglycidyl ether can be directly treated by the invention finishing process for recovery of a low-chlorine fraction of the diglycidyl ether. The crude diglycidyl ether from the condensation reaction is dissolved in an organic solvent at a temperature above about 60° C. In either embodiment (with or without a dehydrohalogenation step), the temperature of the solution of the epoxy resin is then reduced to a level at which solid resin crystallizes from the solution. The optimum temperature of crystallization will vary depending upon the resin, but solid resin will generally begin to crystallize at about 60° C., with higher yields achievable within the range of about 50° C. to about 25° C. The solution can simply be permitted to cool to room temperature, or more rapid cooling can be effected by refrigeration, heat exchange, etc. Highest yields of low-chlorine resin can be achieved by permitting the solution to cool slowly to about 40° C., stirring at this temperature for 2-5 hours, and then stirring at about 25° C. for an additional 4 to 8 hours. It may be desirable to seed the solution with a crystalline material such as previously-recovered epoxy resin. The crystalline epoxy resin can be recovered by filtration or centrifugation. The recovered crystalline polyglycidyl epoxy resin typically has a chlorine content below about 500 ppm, optimally below about 300 ppm, and can be recovered at yields as high as about 40-60 percent. The remaining solution can be treated by conventional means, such as distillation under vacuum, for recovery of an epoxy resin for use in applications with less demanding requirements for low chlorine content.

EXAMPLE 1

An experiment was performed to compare the chlorine levels of 2,2',6,6'-tetramethyl-4,4'-glycidyloxybiphenyl prepared using conventional evaporation recovery with an epoxy resin recovered using the invention process. Into a 5000-ml 4-neck flask equipped with a stirrer, thermocouple, condenser, nitrogen inlet, heating mantle and addition funnel were charged the following:

| | |
|---|---|
| tetramethyl biphenol (g) | 242 |
| epichlorohydrin (g) | 1850 |
| isopropyl alcohol (g) | 1080 |
| water (g) | 313.7 |

The reaction mixture was heated to 70° C., and 20% aqueous NaOH was added in three separate increments of 200 g, 160 g and 80 g, each increment added over a period of one hour. After the final addition was complete, the reaction mixture was held at 70° C. for 30 minutes, and brine was removed by siphon. The reaction mixture was then rotovapped at 150° C. to remove excess epichlorohydrin and solvent.

The dry product was dehydrohalogenated by dissolving in methyl isobutyl ketone solvent and adding 1500 ml of 5% aqueous NaOH in a 5000 ml 4-neck flask equipped with stirrer, thermocouple, condenser, nitrogen inlet and heating mantle. The reaction mixture was heated to reflux temperature (about 92° C.) and held for 2 hours. The brine was removed and the remaining reaction mixture was water-washed with hot tap water four times, with removal of the brine layer each time.

The reaction mixture was divided into two batches. The comparison batch was rotovapped to dryness at 150° C. The invention batch was allowed to cool to room temperature overnight, and crystallized product was recovered, filtered, washed with hexane and dried in a vacuum oven at 50° C. overnight. The weight per epoxide (WPE) and total chlorine content of each sample were determined. Results are shown in Table 1.

TABLE 1

| | WPE | Total Cl (ppm) | Yield |
|---|---|---|---|
| Comparison product | 184 | 1600 | 95 |
| Crystallized product | 181 | 370 | 12 |

As can be seen in Table 1, the product obtained by crystallization had a substantially lower chlorine content than that obtained by solvent distillation, without significant reduction of WPE.

EXAMPLE 2

An experiment was done to increase the yield of crystalline resin obtained by the invention process. To a 5000-ml, four-neck flask equipped as in Example 1 were added 242 g of 2,2',6,6'-tetramethyl-4,4'-dihydroxybiphenyl, 1850 g epichlorohydrin, 1080 g isopropyl alcohol and 313.7 g water. The reaction mixture was heated to 70° C. and 20% NaOH was added in these increments of 200 g, 160 g and 80 g, each added over a one-hour period. The reaction mixture was then held at 70° C. for 30 minutes, and brine was removed by siphon. The reaction mixture was rotovapped at 150° C. to remove excess epichlorohydrin and solvent.

The dry product was then dissolved in methyl isobutyl ketone and dehydrochlorinated by treatment with 1000 ml of 5% NaOH in a 5000 ml, four-neck flask equipped with stirrer, thermocouple, condenser, nitrogen inlet and heating mantle. The reaction mixture was heated to reflux temperature (about 92° C.) and held for about 3.5 hrs. The brine was removed and the remaining reaction mixture was water-washed with hot tap water four times, with brine removal each time. The reaction mixture was dried over magnesium sulfate. The product was filtered and returned to the reaction flask, which was then heated to 80° C. The temperature of the solution was gradually lowered from 80° C. to 40° C. with gentle stirring over a three-hour period. The solution was stirred overnight without added heat and was allowed to cool to room temperature, during which time 157 g of solid resin crystallized from the solution. The crystalline product was filtered, washed with hexane and dried in a vacuum oven at 60° C. overnight.

The product had a WPE of 180 and a total chlorine content of 130 ppm. The recovery of 157 g represented a yield of 44%.

We claim:

1. A process for preparing a diglycidyl ether of a biphenol, the process comprising the steps of:
   (a) contacting, in a reaction mixture at a temperature within the range of about 60° C. to about 110° C., epichlorohydrin and a biphenol which can be represented by the formula

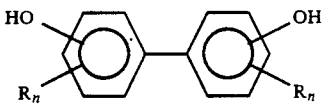

in which each R is independently selected from hydrogen, $C_{1-5}$ alkyl and halide and n is a number within the range of 0 to 4, in the presence of a basic condensation catalyst to produce a reaction product mixture comprising unreacted epichlorohydrin, by-product salt and a diglycidyl ether of the biphenol;
   (b) removing unreacted epichlorohydrin and salt from said reaction product mixture;
   (c) dissolving the remaining crude diglycidyl ether in an organic solvent at a temperature of at least about 60° C.;
   (d) reducing the temperature of said solution to effect crystallization of a relatively low-chlorine fraction of said diglycidyl ether; and
   (e) recovering a crystallized diglycidyl ether.

2. The process of claim 1 in which the organic solvent of step (c) is selected from ketones, alcohols and aromatic hydrocarbons.

3. The process of claim 1 in which the organic solvent of step (c) comprises a ketone.

4. The process of claim 1 in which the organic solvent comprises at least one of methyl ethyl ketone and methyl isobutyl ketone.

5. The process of claim 1 in which the R moiety of the biphenol is selected from hydrogen and methyl.

6. The process of claim 3 in which the biphenol is selected from 4,4'-dihydroxybiphenyl, 3,3'-dimethyl-4,4'-dihydroxybiphenyl and 3,3',5,5'-tetramethyl-4,4'-dihydroxybiphenyl.

7. The process of claim 1 in which the diglycidyl ether comprises the diglycidyl ether of 3,3',5,5'-tetramethyl-4,4'-dihydroxybiphenyl.

8. The process of claim 3 in which the temperature reduction of step (d) is accompanied by stirring of the solution.

9. The process of claim 3 in which the crystallized polyglycidyl ether has a total chlorine content less than about 500 ppm.

10. A process for preparing a diglycidyl ether of a biphenol, the process comprising:
    (a) contacting, in a reaction mixture at a temperature within the range of about 60° C. to about 110° C., epichlorohydrin and a biphenol which can be represented by the formula

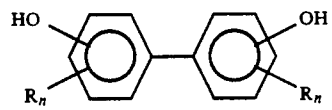

in which each R is independently selected from hydrogen, $C_{1-5}$ alkyl and halide and n is a number within the range of 0 to 4, in the presence of a basic condensation catalyst to produce a reaction product mixture comprising unreacted epichlorohydrin, by-product salt and a diglycidyl ether of the biphenol;
    (b) removing unreacted epichlorohydrin and salt from said reaction product mixture;
    (c) dissolving the remaining crude diglycidyl ether in an organic solvent and contacting said crude diglycidyl ether with a dehydrochlorination agent for a time of at least about 0.5 hour to produce a dehydrochlorination product mixture comprising the diglycidyl ether in solution;
    (d) reducing the temperature of said solution to effect crystallization of a relatively low-chlorine fraction of said diglycidyl ether; and
    (e) recovering the crystallized diglycidyl ether.

11. The process of claim 10 in which the organic solvent of step (c) comprises at least one of a ketone, alcohol, aliphatic hydrocarbon and aromatic hydrocarbon.

12. The process of claim 10 in which the organic solvent comprises a ketone.

13. The process of claim 10 in which the organic solvent comprises at least one of methyl ethyl ketone and methyl isobutyl ketone.

14. The process of claim 12 in which the R moiety of the biphenol is selected from hydrogen and methyl.

15. The process of claim 12 in which the diglycidyl ether is a diglycidyl ether of 2,2',6,6'-tetramethyl-4,4'-dihydroxybiphenyl.

16. The process of claim 12 in which the dehydrochlorination agent is sodium hydroxide.

17. The process of claim 16 in which the temperature reduction step (c) is accompanied by stirring of the solution.

18. The process of claim 10 in which step (c) is carried out at a temperature of at least about 60° C.

19. A process for preparing a diglycidyl ether of a biphenol having a chlorine content less than about 500 ppm, the process comprising the steps of:
    (a) dissolving a crude diglycidyl ether of a biphenol having a chlorine content greater than about 1000 ppm in an organic solvent and contacting said crude diglycidyl ether at an elevated temperature with a base for a time of at least about 0.5 hour to produce a dehydrochlorination product mixture comprising the diglycidyl ether in solution; and
    (b) reducing the temperature of said solution to effect solidification of said diglycidyl ether in a crystalline form having a chlorine content less than about 500 ppm.

20. The process of claim 19 in which the base of the step (a) is sodium hydroxide and the contacting is carried out at a temperature within the range of about 60° to about 110° C.

21. The process of claim 20 in which the organic solvent comprises a ketone.

22. The process of claim 21 in which the organic solvent comprises at least one of methyl ethyl ketone and methyl isobutyl ketone.

23. The process of claim 22 in which the diglycidyl ether is the diglycidyl ether of 2,2',6,6'-tetramethyl-4,4'-dihydroxybiphenyl.

24. The process of claim 23 in which the reduction in temperature of the solution is accompanied by stirring of the solution.

* * * * *